United States Patent
Natsuaki et al.

(10) Patent No.: US 10,197,658 B2
(45) Date of Patent: Feb. 5, 2019

(54) METHODS, SYSTEMS AND APPARATUSES FOR USING FLEXIBLE TRIGGERED SEGMENTATION TO OPTIMIZE MAGNETIC RESONANCE IMAGING

(71) Applicant: Siemens Healthcare GmbH, Erlangen (DE)

(72) Inventors: Yutaka Natsuaki, Riverside, CA (US); Randall Kroeker, Winnipeg (CA); Gerhard Laub, San Mateo, CA (US); Peter Schmitt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 597 days.

(21) Appl. No.: 14/329,259

(22) Filed: Jul. 11, 2014

(65) Prior Publication Data

US 2015/0038829 A1 Feb. 5, 2015

Related U.S. Application Data

(60) Provisional application No. 61/861,633, filed on Aug. 2, 2013.

(51) Int. Cl.
*A61B 5/05* (2006.01)
*G01R 33/567* (2006.01)
(Continued)

(52) U.S. Cl.
CPC ........ *G01R 33/5673* (2013.01); *A61B 5/0044* (2013.01); *A61B 5/055* (2013.01);
(Continued)

(58) Field of Classification Search
None
See application file for complete search history.

(56) References Cited

U.S. PATENT DOCUMENTS 5,830,143 A * 11/1998 Mistretta .............. G01R 33/561
324/306
6,198,959 B1 * 3/2001 Wang .................... A61B 5/055
324/307

(Continued)

FOREIGN PATENT DOCUMENTS

JP 2001-178700 A 7/2001
JP 2004-024783 A 1/2004
(Continued)

OTHER PUBLICATIONS

Natsuaki, et al., A Novel Adaptive Approach to the Steady-State Triggering for the ECG-Gated Contrast-Enhanced MR Angiography, Presented at 25th International Workshop on Magnetic Resonance Angiography (New York), on Aug. 20-23, 2013, 2 pages.

(Continued)

*Primary Examiner* — Joel F Brutus

(57) ABSTRACT

A method for using flexible triggered segmentation to optimize magnetic resonance imaging includes partitioning a k-space table into a plurality of k-space segments, each respective k-space segment comprising one or more phase-encoding steps from a plurality of slice-encoding lines. A cardiac cycle is monitored using an electrical signal tracking system and used to trigger acquisition of the plurality of k-space segments over a plurality of acquisition windows.

18 Claims, 12 Drawing Sheets

(51) Int. Cl.
  *A61B 5/055* (2006.01)
  *G01R 33/48* (2006.01)
  *A61B 5/00* (2006.01)
  *G01R 33/56* (2006.01)

(52) U.S. Cl.
  CPC ........ *A61B 5/7292* (2013.01); *G01R 33/4818* (2013.01); *A61B 2576/023* (2013.01); *G01R 33/5601* (2013.01)

(56) References Cited

U.S. PATENT DOCUMENTS

| | | | |
|---|---|---|---|
| 8,200,311 | B2 | 6/2012 | Spincemaille et al. |
| 2003/0184291 | A1* | 10/2003 | Rehwald ............ G01R 33/5673 324/307 |
| 2004/0061496 | A1 | 4/2004 | Ookawa |
| 2005/0071110 | A1* | 3/2005 | Davis ............... G01N 35/00732 702/123 |
| 2007/0078331 | A1* | 4/2007 | Cull ................... G01R 33/5601 600/410 |
| 2009/0302840 | A1* | 12/2009 | Fung ................. G01R 33/4818 324/309 |
| 2010/0079141 | A1* | 4/2010 | Stemmer ............ G01R 33/4824 324/309 |

FOREIGN PATENT DOCUMENTS

| | | |
|---|---|---|
| JP | 2011-072448 A | 4/2011 |
| JP | 2014-073357 A | 4/2014 |
| WO | 2005034749 A1 | 4/2005 |
| WO | 2012026380 A1 | 3/2012 |

OTHER PUBLICATIONS

Natsuaki, et al., Advancements in Thoracic ECG-Gated Contrast Enhanced MR Angiography with Flexible Triggered Segmentation, Presented at 24th International Workshop on Magnetic Resonance Angiography, Utrecht, Netherlands on Sep. 19-21, 2012, 2 pages.

Spincemaille, et al, Motion Artifact Suppression in Breath Hold 3D Contrast Enhance Magnetic Resonance Angiography using ECG Ordering, In Engineering in Medicine and Biology Society, 2006. EMBS'06. 28th Annual International Conference of the IEEE, pp. 739-742. IEEE, 2006.

Natsuaki, et al., The Flexible Triggered Segmentation Optimizes Thoracic ECG-Gated Contrast Enhanced MR Angiography, Presented at 21st Annual Meeting and Exhibition of Int'l Society of Magnetic Resonance in Medicine, Salt Lake City, Utah, on Apr. 22-26, 2013, 1 page.

Natsuaki, et al., A Novel Approach to ECG-Gated High Resolution Contrast-Enhanced MR Angiography in a Single Breath Hold, Presented at 22nd International Workshop on Magnetic Resonance Angiography, Seoul, Korea on Oct. 6-8, 2010, 1 page.

Natsuaki, et al., A Novel Approach to ECG-Gated High-Resolutions Contrast-Enhanced MR Angiography in Thorax: Technical Aspects, Presented at 19th Annual Meeting and Exhibition of Int'l Society of Magnetic Resonance in Medicine, Montreal, Quebec, Canada, on May 7-13, 2011, 1 page.

Office Action dated Dec. 19, 2017 received in Corresponding Japanese Application No. 2014-157646, with Translation.

* cited by examiner

If $D_{acq} \geq Ce$

No changes are required; just acquire them in linear ascending fashion.

If $D_{acq} < Ce$ (1) Acquire linearly from {Ce+$D_{acq}$} to min [Ce+$D_{acq}$, N(at max border)], then (2) acquire centric out from there If $D_{acq} > Ce$ (1) Acquire around the maximum border until currentOrder = $D_{acq}$ - Ce, then (2) linearly acquire from the minimum border

METHODS, SYSTEMS AND APPARATUSES FOR USING FLEXIBLE TRIGGERED SEGMENTATION TO OPTIMIZE MAGNETIC RESONANCE IMAGING

CROSS-REFERENCE TO RELATED APPLICATIONS

This application claims priority to U.S. provisional application Ser. No. 61/861,633 filed Aug. 2, 2013, which is incorporated herein by reference in its entirety.

TECHNICAL FIELD

The present invention relates generally to methods, systems, and apparatuses for using flexible triggered segmentation to optimize Magnetic Resonance Imaging (MRI). The disclosed methods, systems, and apparatuses may be applied to, for example, improve image quality in ECG-gated, contrast enhanced MRI applications.

BACKGROUND

For most of the current contrast-enhanced MR angiography (CE-MRA) examinations in the healthcare industry, acquisition is optimized for image contrast enhancement by matching the contrast arrival timing with the acquisition of the central phase encoding steps (i.e., time-to-center, TTC). The total scan time is kept short within a breath-hold length to suppress bulk breathing motion. Typically, the CE-MRA data are acquired without ECG-gating in a single continuous delayed centric trajectory. For most purposes, this approach is satisfactory. However, in CE-MRA of the thorax, the cardiac chambers and ventricular outflow vessels can be delineated with a certain degree of blurring with non-gated acquisition. To address this limitation, CE-MRA can be acquired with electrocardiography (ECG) gating, whereby the segmented data acquisition is synchronized with the cardiac cycle.

Conventional CE-MRA sequences support ECG gating with rigid trigger segmentation. For every trigger pulse, the conventional gated CE-MRA acquires all phase encoding steps for a single value of the slice encoding gradient. The acquisition is then repeated in linear order for all slice encoding values. With a suitable trigger delay (TD), the center of k-space in the inner loop (i.e. phase-encoding) direction (ky=0) can be acquired outside of the systolic phase, where the cardiac motions are most prominent. With proper contrast injection timing, the arterial window can still be matched with the center of the k-space in the outer loop (i.e. slice encoding) direction. With this scheme, the total scan time corresponds to the average R-R interval multiplied by the total number of slice encoding steps.

The conventional gated CE-MRA has two major unfulfilled needs. First, due to the rigid segmentation structure, the scan is very inefficient. For example, a typical high-resolution non-gated CE-MRA protocol uses short TR times of 2.7 ms and less than 200 phase encode steps in ky direction. Hence, the data acquisition window during each heartbeat is much shorter than the average R-R interval, which reduces the efficiency of the acquisition. Furthermore, the conventional gated CE-MRA technique cannot reduce scan time by taking advantage of parallel acquisition techniques (e.g., iPAT) and partial Fourier in phase encoding direction; if either of these parameters is modified, the total scan time remains the same since conventional CE-MRA only a single complete inner loop is played out per heartbeat, regardless of its duration. Secondly, the unpredictable nature of the in-vivo ECG-triggering adds some uncertainty to the gated CE-MRA. While the sequence assumes a steady R-R interval and uses a fixed acquisition window, due to physiological irregularities (e.g., the R-R interval can vary during a breath-hold) and mechanical imperfections (e.g., ECG detection device can fail), trigger events can be either detected too early or too late to substantially increase the scan time. Moreover, the CE-MRA sequence has a strict timing requirement with the contrast arrival, and any deviation from this may result in a contrast washout with missed optimal timing.

SUMMARY

Embodiments of the present invention address and overcome one or more of the above shortcomings and drawbacks, by providing methods, systems, and apparatuses that use flexible triggered segmentation to optimize magnetic resonance imaging. This technology is particularly well-suited for, but by no means limited to, improving image quality in ECG-gated, contrast enhanced Magnetic Resonance Imaging (MRI) applications.

According to some embodiments of the present invention, a method for using flexible triggered segmentation to optimize magnetic resonance imaging includes partitioning a k-space table into a plurality of k-space segments, each respective k-space segment comprising one or more phase-encoding steps from a plurality of slice-encoding lines. A cardiac cycle is monitored using an electrical signal tracking system and used to trigger acquisition of the plurality of k-space segments over a plurality of acquisition windows. In some embodiments, a time-to-center value is received from a user interface. The acquisition of each respective k-space segment may then be timed such a center point of the respective k-space segment occurs at the time-to-center value.

The k-space table may be partitioned, for example by applying a segmentation generation function and a scaling algorithm to the segmentation generation table to yield a modified k-space table. The k-space segments may then be created by selecting a predetermined number of elements (e.g., selected by the user) from the modified table. Various scaling algorithms may be used within the scope of the present invention. For example, in one embodiment, the scaling algorithm includes multiplying each respective element of the table by a predetermined multiplicator value and then adding a pseudo-random number to each respective element.

In some embodiments a center k-space segment corresponding to lines close to k-space center is selected from the plurality of k-space segments. This selection may be performed, for example based on a user's identification of a particular segment. Alternatively, a center k-space segment may be automatically selected, for example, based on timing of a contrast injection.

Various trigger adjustment processes may be applied with the aforementioned method. For example, in some embodiments, each respective window is associated with a trigger delay value which may be adjusted to compensate for early or late triggers during the acquisition window. Thus, for example, following each respective acquisition window, an early trigger adjustment process may be performed. This process may include, for example, determining whether a trigger event occurred during the respective acquisition window. If the trigger event occurred, a missed trigger time value is then determined based on a current time value and the timing of the trigger event. If this missed trigger time value is less than or equal to the trigger delay value for that window, the trigger delay value associated with a subsequent acquisition window is adjusted. Similarly, if a subsequent trigger event does not occur within a predetermined maximum wait time, a subsequent acquisition window may be automatically initiated. Following the subsequent acquisition window, if the next trigger event does not occur within the predetermined maximum wait time, the trigger delay value associated with the acquisition windows may be reduced to a predetermined minimal value.

According to other embodiments of the present invention, a method for using flexible triggered segmentation to optimize magnetic resonance imaging includes determining a plurality of k-space segments, where each respective k-space segment includes data from multiple dimensions of k-space. A linear-centric reordering process is applied to the k-space segments such that a desired center k-space segment will be acquired during a diastolic phase of a patient's cardiac cycle. Then, the k-space segments may be acquired over a plurality of acquisition windows, with each acquisition window being triggered based on the cardiac cycle.

According to another embodiment of the present invention, a system for using flexible triggered segmentation to optimize magnetic resonance imaging includes an image data processor, an electrocardiography device, and a Radio Frequency (RF) generator. The image data processor is configured to partition a k-space table into a plurality of k-space segments, with each respective k-space segment comprising one or more phase-encoding steps from a plurality of slice-encoding lines. The electrocardiography device is configured to monitor a cardiac cycle using an electrical signal tracking system. The RF generator is configured to acquire the plurality of k-space segments over a plurality of acquisition windows, wherein each acquisition window is triggered based on the cardiac cycle.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The present invention relates generally to methods, systems, and apparatuses for using flexible triggered segmentation to optimize magnetic resonance imaging. This technology is particularly well-suited for, but by no means limited to, improving image quality in ECG-gated, contrast enhanced Magnetic Resonance Imaging (MRI) applications. For example, using some embodiments of the techniques described herein, cardiac motion suppressed ECG-gated CE-MRA can be realized without compromises in higher spatial resolution or the scan duration (efficient enough to complete the scan within a single breath hold and has added confidence in ECG performance).

Figure 1:
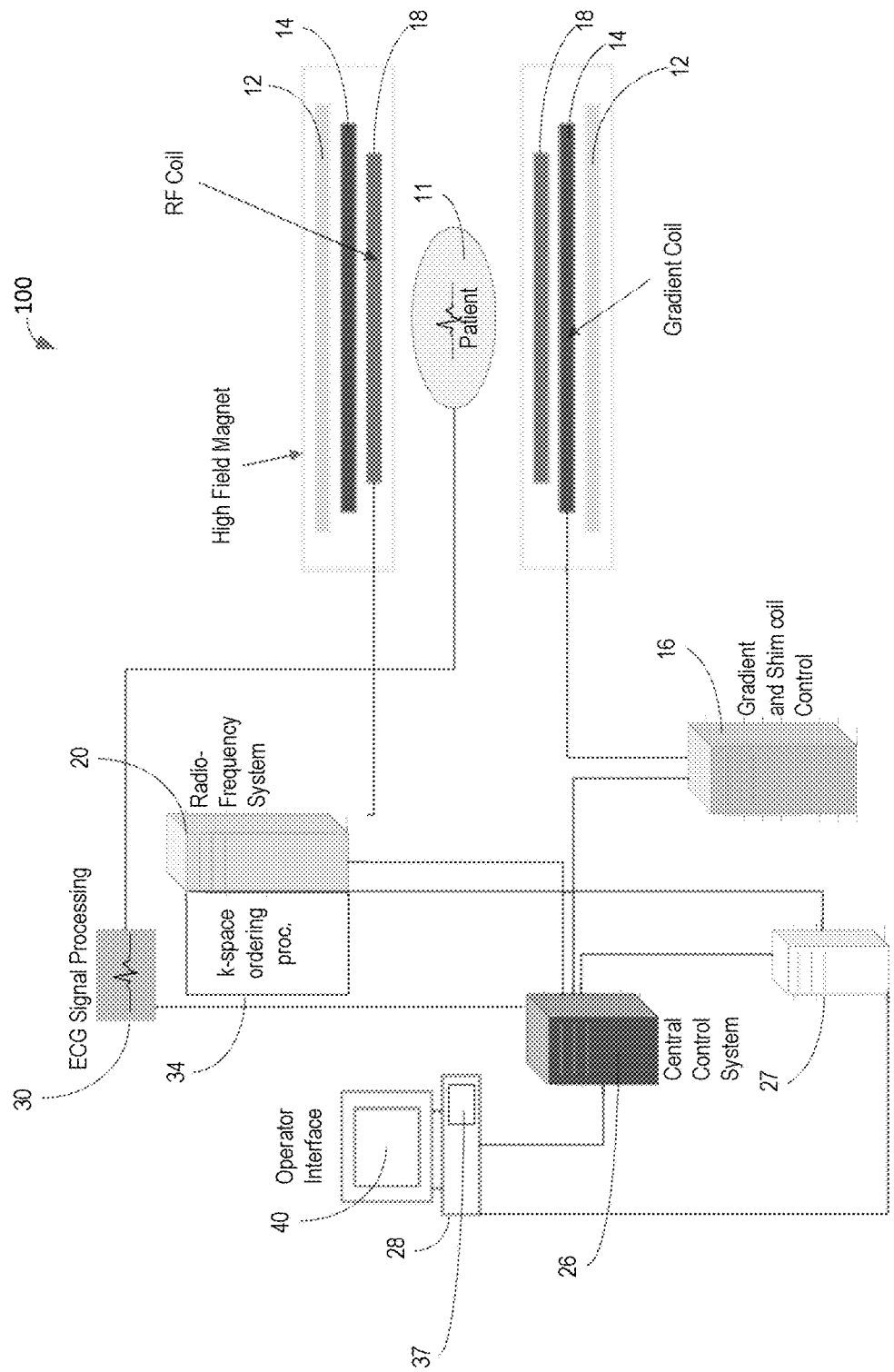
FIG. 1 shows system for ordering acquisition of frequency domain components representing MR image data for storage in a k-space storage array, as may be used in some embodiments of the present invention.

FIG. 1 shows system 100 for ordering acquisition of frequency domain components representing MR image data for storage in a k-space storage array, as may be used in some embodiments of the present invention. In system 100, magnet 12 creates a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shimming and pulse sequence control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further, Radio Frequency (RF) module 20 provides RF pulse signals to RF coil 18, which in response produces magnetic field pulses which rotate the spins of the protons in the patient 11 by ninety degrees or by one hundred and eighty degrees for so-called "spin echo" imaging, or by angles less than or equal to 90 degrees for so-called "gradient echo" imaging. Pulse sequence control module 16 in conjunction with RF module 20 as directed by central control unit 26, control slice-selection, phase-encoding, readout gradient magnetic fields, radio frequency transmission, and Magnetic Resonance signal detection, to acquire Magnetic Resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide image representative data to an image data processor. In some embodiments, the image data processor is located in central control unit 26, while in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in unit 34 stores corresponding individual frequency components comprising an MR dataset. The k-space array of individual data elements has a designated center and individual data elements which each have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and the magnetic field gradient change between successively acquired frequency components is substantially minimized.

Central control unit 26 uses information stored in an internal database to process the detected MR signals in a coordinated manner to generate high quality images of a selected slice (or slices) of the body and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40. Computer 28 includes a graphical user interface (GUI) enabling user interaction with central control unit 26 and enables user modification of Magnetic Resonance imaging signals in substantially real time. Display processor 37 processes the Magnetic Resonance signals to provide image representative data for display on display 40, for example.

Figure 2:
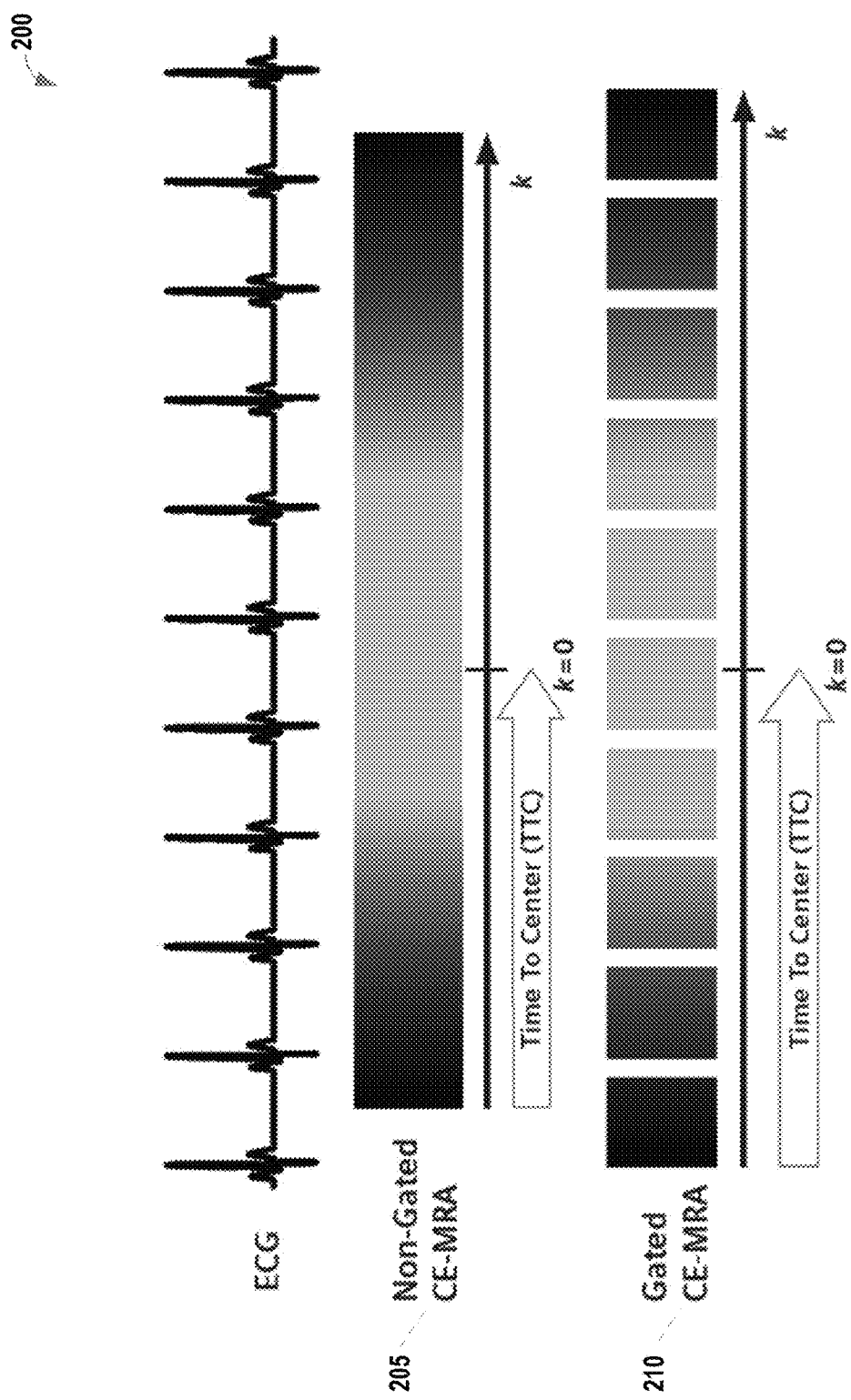
FIG. 2 provides a comparison of non-gated CE-MRA versus gated CE-MRA.
Figure 3:
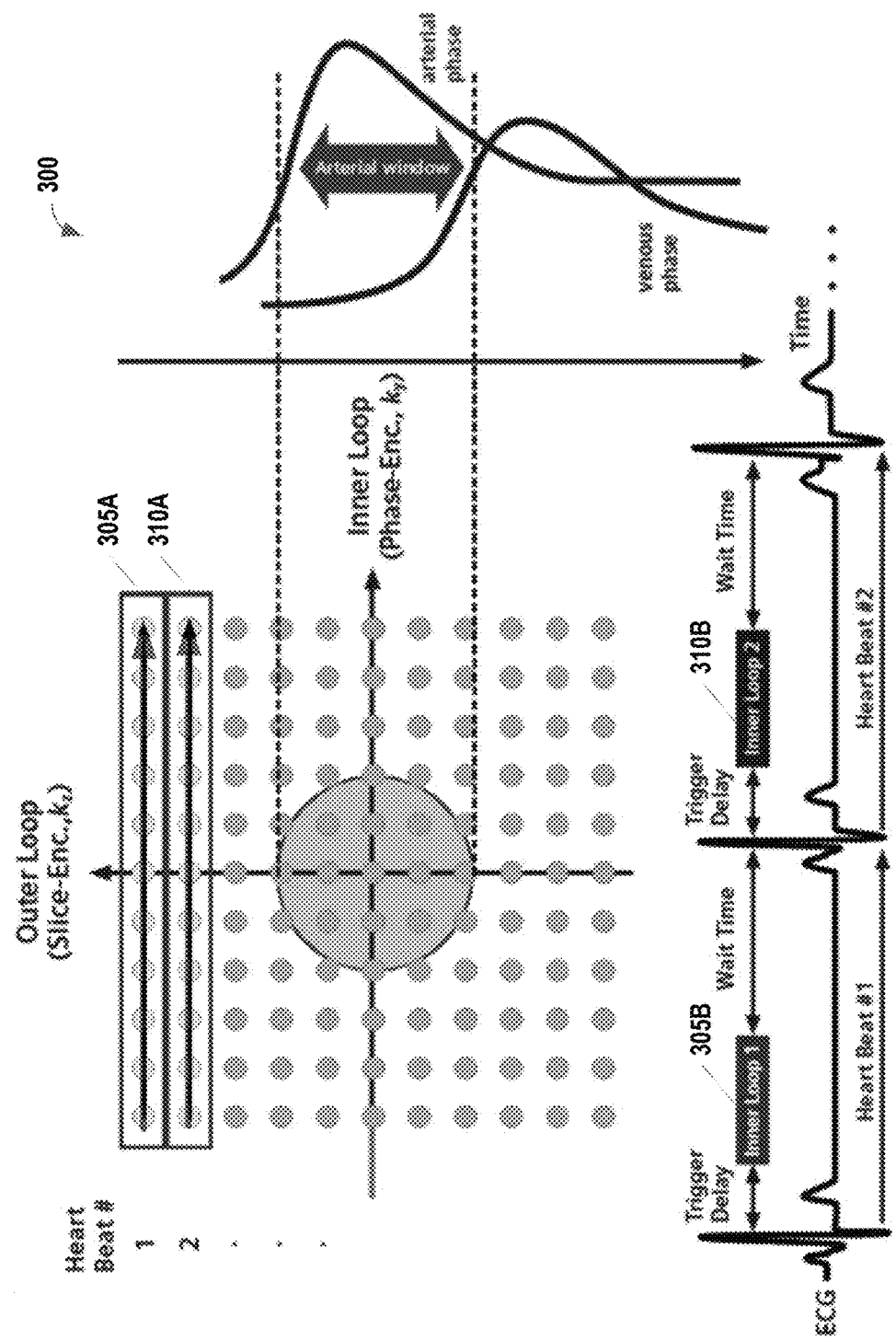
FIG. 3 illustrates a rigid trigger segmentation process relied upon by some convention systems.

The system 100 described in FIG. 1 may be applied to image blood vessels using a technique referred to as contrast-enhanced MR angiography (CE-MRA). In cardiac applications where movement may blur acquired images, the CE-MRA is preferably applied with ECG-gating. However, the addition of gating introduces some complexity regarding how the acquisition is segmented with respect to the ECG signal. FIG. 2 provides an illustration 200 comparing non-gated CE-MRA 205 versus gated CE-MRA 210. The darker gray color bar represents the outer k-space in both phase (ky) and slice (kz) encoding steps, and the lighter gray represents the inner k-space. The center of both phase and slice encoding steps (ky=0, kz=0) is represented by k=0. As shown, in CE-MRA, the contrast arrival timing typically is matched with the center acquisition of the phase and slice encoding steps (i.e., considering the time-to-center, TTC) for the optimal image contrast. For non-gated CE-MRA 205, the data is acquired in a single continuous delayed centric trajectory, where phase and slice encoding steps start from the outer k-space, then acquire inner k-space & k=0, and finally the rest of the outer k-space to complete the scan. Conversely, for the gated CE-MRA 210, the acquisition is segmented and acquired in sync with the ECG-triggering. This segmentation reduces the blurring that results from cardiac movement. However, conventional systems rely upon the rigid trigger segmentation process 300 illustrated in FIG. 3. For each trigger pulse of the ECG (i.e., each heartbeat), all phase-encoding steps of a single slice-encoding line are acquired. Note that the data acquisition windows (e.g., 305A/305B, 310A/310B) during each heartbeat are much shorter than the average R-R interval (i.e., heartbeat). As a result, the acquisition is very inefficient.

Figure 4:
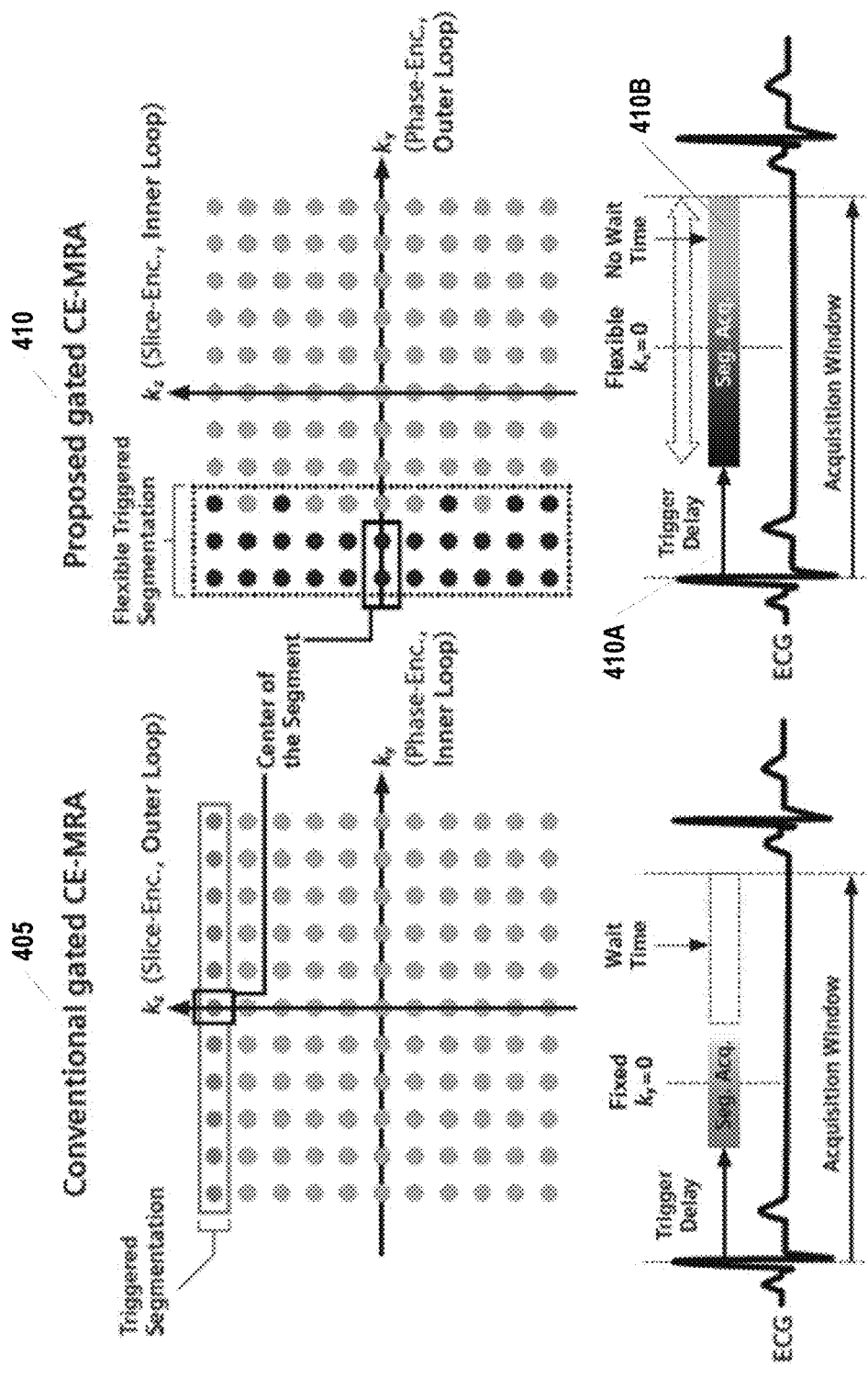
FIG. 4 provides a comparison of the conventional gated CE-MRA with rigid triggered segmentation process versus the gated CE-MRA with flexible triggered segmentation process, as may be implemented according to some embodiments of the present invention.

Described herein is a flexible trigger segmentation process that may be used to improve the efficiency of the rigid trigger segmentation in conventional gated CE-MRA. Using this process, the inner loop is not restricted to a single dimension in k-space. The points that are sampled within the individual triggered segments are determined with a fuzzy pseudo-random algorithm (described below). As a result, the size and shape of the triggered segments are no longer restricted. FIG. 4 provides a comparison of the conventional gated CE-MRA with rigid triggered segmentation process 405 versus the proposed gated CE-MRA with flexible triggered segmentation process 410, as may be implemented according to some embodiments of the present invention. The flexible triggered segmentation can fill in any unnecessary wait time after the data acquisition window (seq. acq.) 410B, and thus providing more efficiency than the convention technique. Note that even with the proposed flexible triggered segmentation, the total efficiency may still be less than 100% due to the trigger delay 410A needed for avoiding cardiac motion during systolic phase. As an additional means of achieving further cardiac motion suppression, the center of the triggered segments can be specified with the flexible triggered segments. This may be contrasted with the rigid triggered segment which will be fixed somewhere in the middle of the acquisition window.

In some embodiments, the fuzzy pseudo-random algorithm used in the flexible trigger segmentation process is implemented as follows. For given k-space table elements (e.g., ky-kz map) with assigned location element number, segmentation of the size N can be achieved by calculating the segmentation generating function and select N elements in the ascending order. The segmentation generating function may generate multiple table elements with the same value. For example, the following 3×10 table elements utilize the row indices (e.g., 0, 1 and 2) as the segmentation generation function:

| 0 | 0 | 0 | 0 | 0 | 0 | 0 | 0 | 0 | 0 |
|---|---|---|---|---|---|---|---|---|---|
| 1 | 1 | 1 | 1 | 1 | 1 | 1 | 1 | 1 | 1 |
| 2 | 2 | 2 | 2 | 2 | 2 | 2 | 2 | 2 | 2 | and has assigned location element number with:

| 0  | 1  | 2  | 3  | 4  | 5  | 6  | 7  | 8  | 9  |
|----|----|----|----|----|----|----|----|----|----|
| 10 | 11 | 12 | 13 | 14 | 15 | 16 | 17 | 18 | 19 |
| 20 | 21 | 22 | 23 | 24 | 25 | 26 | 27 | 28 | 29 |

In these cases, it can happen that N of these elements must be assigned to segment A while the rest of the elements must be assigned to another segment B. Splitting up the example table into 2 segments of equal size (N=15) with location element number as a tie-breaker, results in the following table:

| A | A | A | A | A | A | A | A | A | A |
|---|---|---|---|---|---|---|---|---|---|
| A | A | A | A | A | B | B | B | B | B |
| B | B | B | B | B | B | B | B | B | B |

It is evident that this segmentation is quite "unbalanced" in the 2nd row, since the center of segment A is shifted to the left, while the center of B is shifted to the right.

In order to balance the segmentation, fuzzy scaling may be applied to the original segmentation generation function table. In some embodiments, this fuzzy scaling may be applied according to the following formula:

```
for (x=0; x < MaxElements; x++)
{
    NewTable[x] = M * SegTable [x] + ((100 + x) * StdE) % M);
}
``` where x=element location number (0-MaxElements-1), SegTable[x]=the original segmentation generation function table, and two constants multiplicator M and standard expansion (StdE). Intuitively in above example, the original segmentation generation function table is multiplied first with a multiplicator (e.g., M=3) and "pseudo random numbers" are added to each element (e.g., between 0 and 2). Thus, the following modified segmentation generation function table may be generated:

| 0 | 0 | 2 | 0 | 1 | 1 | 2 | 0 | 1 | 2 |
|---|---|---|---|---|---|---|---|---|---|
| 5 | 3 | 3 | 4 | 5 | 3 | 5 | 4 | 5 | 3 |
| 8 | 7 | 6 | 7 | 7 | 6 | 8 | 6 | 6 | 8 |

Doing the segmentation after this pre-processing step yields a more "balanced" segmentation:

| A | A | A | A | A | A | A | A | A | A |
|---|---|---|---|---|---|---|---|---|---|
| B | A | A | A | B | A | B | B | B | A |
| B | B | B | B | B | B | B | B | B | B |

In addition to the scan efficiency improvement, the flexible triggered segmentation can freely adjust the acquisition order (both within and in between segments) with the linear-centric reordering. More specifically, given the fixed number of elements and the center of the element location number in ascending order, linear-centric reordering (described in greater detail below) may be applied to acquire the center element at the desired acquisition order. This additional flexibility leads to further optimization in cardiac motion suppression, contrast timing and user-interface optimizations.

With a flexible size of the triggered shots, the sequence can utilize essentially all of the available time in the acquisition window, which helps to reduce unnecessary wait time. In practice, this alone can improve the scan efficiency of a gated CE-MRA acquisition to values close to 70%, which is more than twice the conventional gated CE-MRA of approximately 30%. Furthermore, the flexible segmentation is compatible with conventional scan time reduction methods such as, for example, parallel imaging (e.g., iPAT), partial Fourier, and elliptical scanning. The rigid trigger segmentation can potentially improve the scan efficiency by acquiring multiple complete phase encoding lines since each trigger segment acquisition are typically far shorter than the RR interval (e.g., as shown in FIG. 4). However, this is still restricted since the in-vivo RR interval can never match to the exact integer multiples of the complete phase encoding lines. Also the scan efficiency varies according to the actual heart rates, and on shorter extreme of the RR interval the gated CE-MRA cannot be performed.

In the conventional gated CE-MRA, only the PE steps for a single partition encoding step are acquired. This corresponds to the comparatively short acquisition duration. In order to reduce the pulsatile cardiac motion, these triggered segment acquisitions may be positioned in diastole (i.e. the quiescent phase with the minimal cardiac motion). With the flexible triggered segmentation process described herein, the time used for each individual triggered segment acquisition may be increased in order to use the RR interval more efficiently. In order to achieve this, flexible reordering may be used that (1) assigns more k-space points to each triggered segments, and (2) makes sure that the most important data points within each shot (lines close to k-space center, $k_z=0$ in FIG. 4) are still acquired in diastole.

Figure 5A:
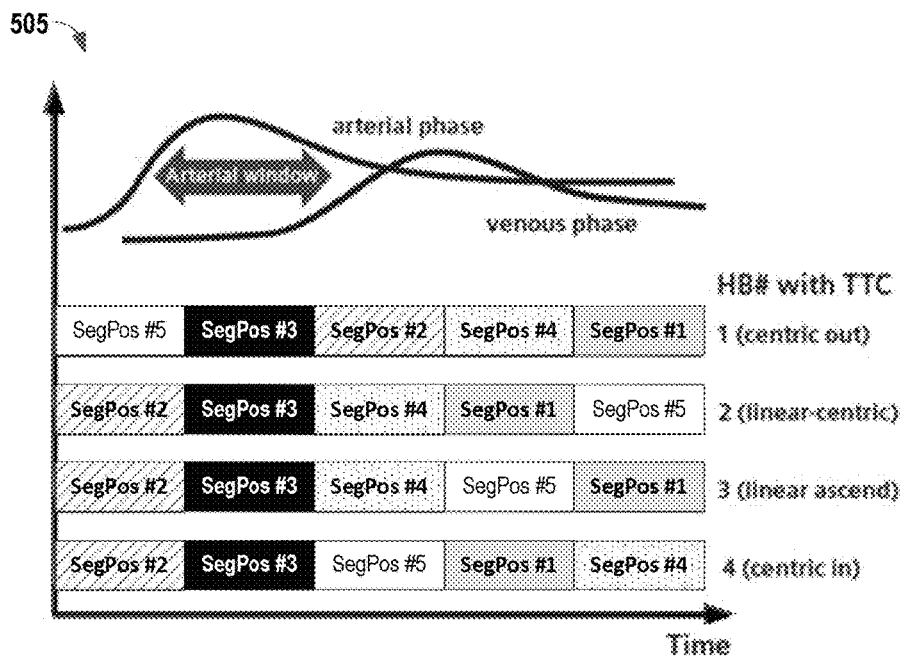
FIGS. 5A and 5B provide illustrations of flexible inter-triggered shot ordering, according to some embodiments of the present invention.
Figure 5B:
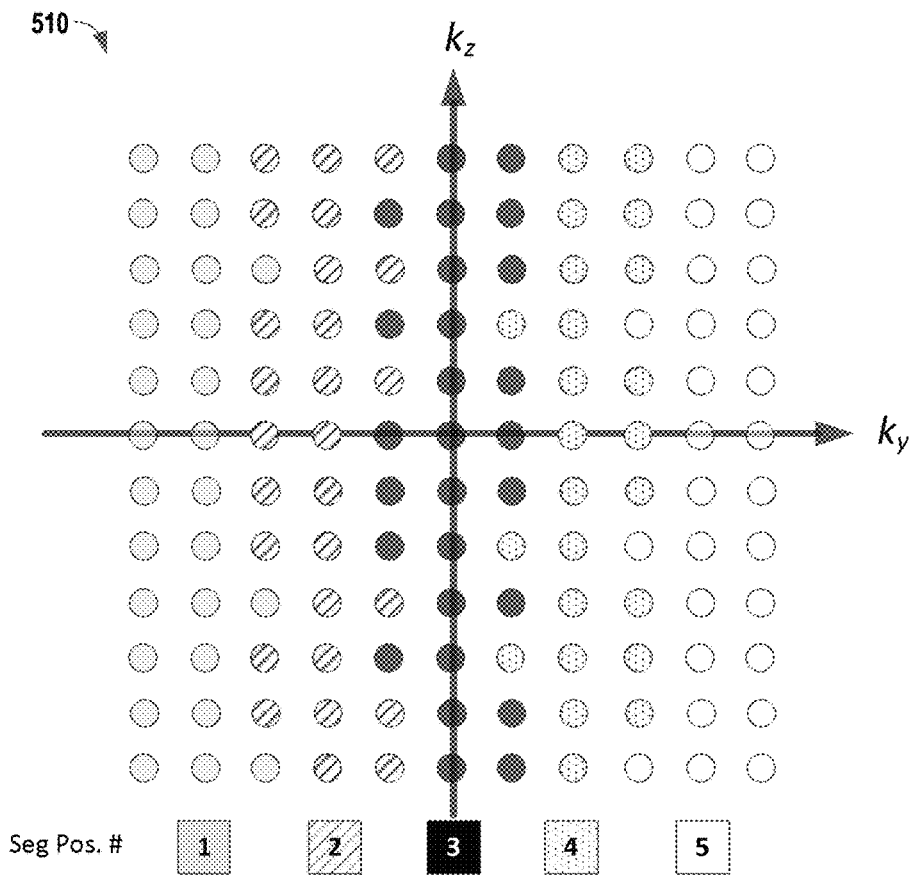

In the proposed sequence, the linear-centric reordering (e.g. combination of linear and centric reordering) enables acquisition in diastole regardless of the size and the shape of the triggered segments. The user interface parameter 'Time-To-Center (TTC) per Heart Beat (HB)' (located on the Sequence Special Card) may be utilized to specify the center of the triggered segment acquisition timing, and this can be set to anywhere within the acquisition window. FIGS. 5A and 5B provide illustrations of flexible inter-triggered shot ordering, according to some embodiments of the present invention. FIG. 5B shows conceptual view 505 of a k-space table where each triggered shot represented by the different pattern on the ky-kz map, each having an assigned segment positioning number in linear ascending order. FIG. 5A shows a tiling chart 510 illustrating the overall triggered shot acquisition timing relative to the contrast injection. The overall TTC is defined as the time from the beginning of the scan to the acquisition of the center positioned segment (e.g., in FIGS. 5A and 5B SegPos#3).

Figure 6A:
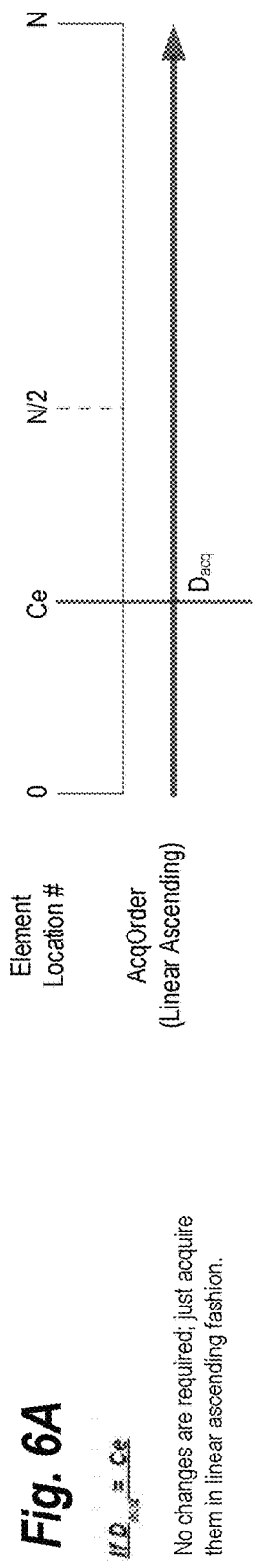
FIGS. 6A, 6B, and 6C illustrate three different reordering algorithms that may be applied with the flexible triggered segmentation, in some embodiments of the present invention.
Figure 6B:
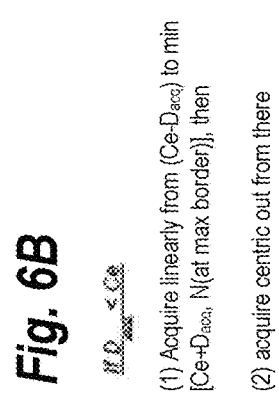
Figure 6C:
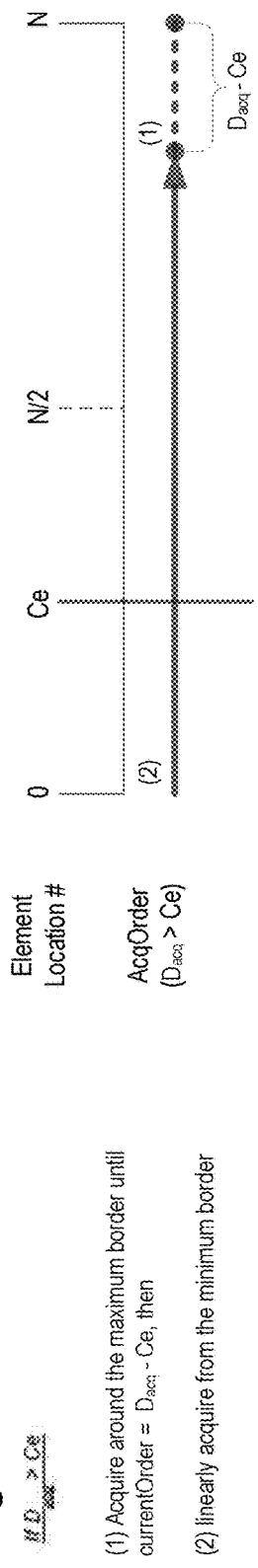

FIGS. 6A, 6B, and 6C illustrate three different reordering algorithms that may be applied with the flexible triggered segmentation, in some embodiments of the present invention. Let N represent the total number of elements, Ce represent the center of elements in terms of element location number (linear ascending), and $D_{acq}$ represent the desired Ce acquisition order. In FIG. 6A, the values of $D_{acq}$ and Ce are equal. No changes are required and acquisitions may occur in a linear ascending fashion. In FIG. 6B, $D_{acq}$ is less than Ce. In this case, acquisitions are made linearly from (Ce−$D_{acq}$) to the minimum of [Ce+ $D_{acq}$, N(at max border)]. After that point, acquisitions are centric. FIG. 6C shows the algorithm for when $D_{acq}$ is greater than Ce. In this instance, acquisitions are made around the minimum border until the current order is equal to $D_{acq}$−Ce. Then, acquisitions are made linearly from the minimum border. Note that if $D_{acq}$ is less than N/2, the order may be reversed while the same algorithms are applied.

The order of the inter trigger shots may also be flexible. For example, in some embodiments, the linear-centric algorithm allows the user to specify when to acquire the triggered shot that encompasses the k-space center (e.g., ky=0, kz=0, Shot-Pos#3 in the example in FIGS. 5A and 5B). In analogy to the "TTC" parameter in the non-gated CE-MRA, a user interface parameter such as "overall TTC" may be used to calculate and adjust the triggered shot ordering to the closest match.

Figure 7:
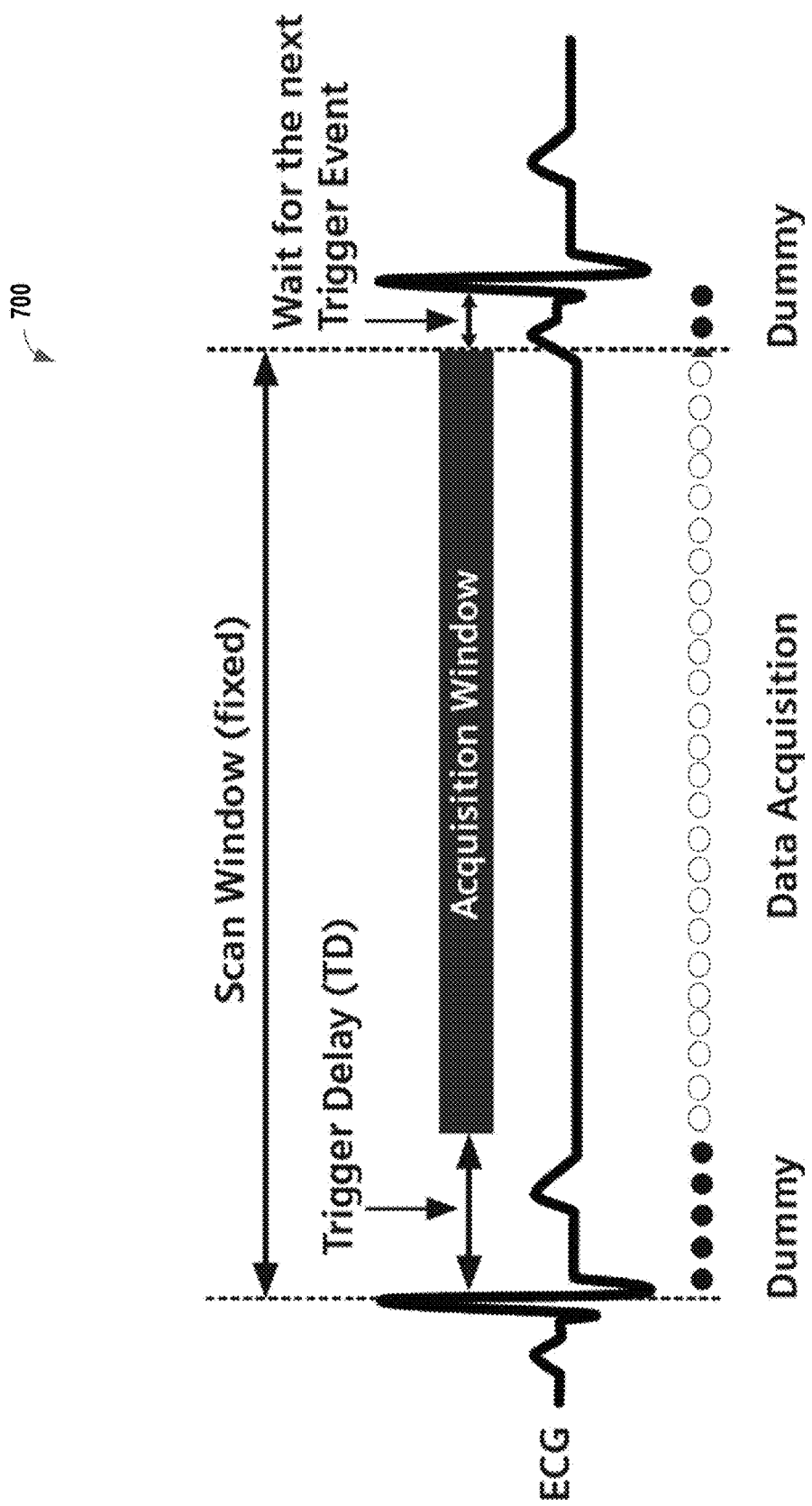
FIG. 7 provides an example illustration of steady state triggering, according to some embodiments of the present invention.

In some embodiments, the proposed gated CE-MRA implements a steady state triggering mechanism (i.e., RF pulses are played out without acquisition during the wait time and the trigger delay) in order to avoid signal variations in the segmented readout. FIG. 7 provides an example illustration 700 of steady state triggering, according to some embodiments of the present invention. In order to maintain the magnetization in the readout (represented as white dots), the steady state triggering continues to play out RF pulses without data acquisition during the wait time and trigger delay (i.e., dummy pulses, represented as black dots). Additionally, in some embodiments, the proposed gated CE-MRA automatically adapts the steady state triggering to compensate some of the commonly occurring trigger issues (i.e. early and late trigger detections). This adaptive steady state triggering ensures that the gated CE-MRA is completed in an efficient manner.

Figure 8:
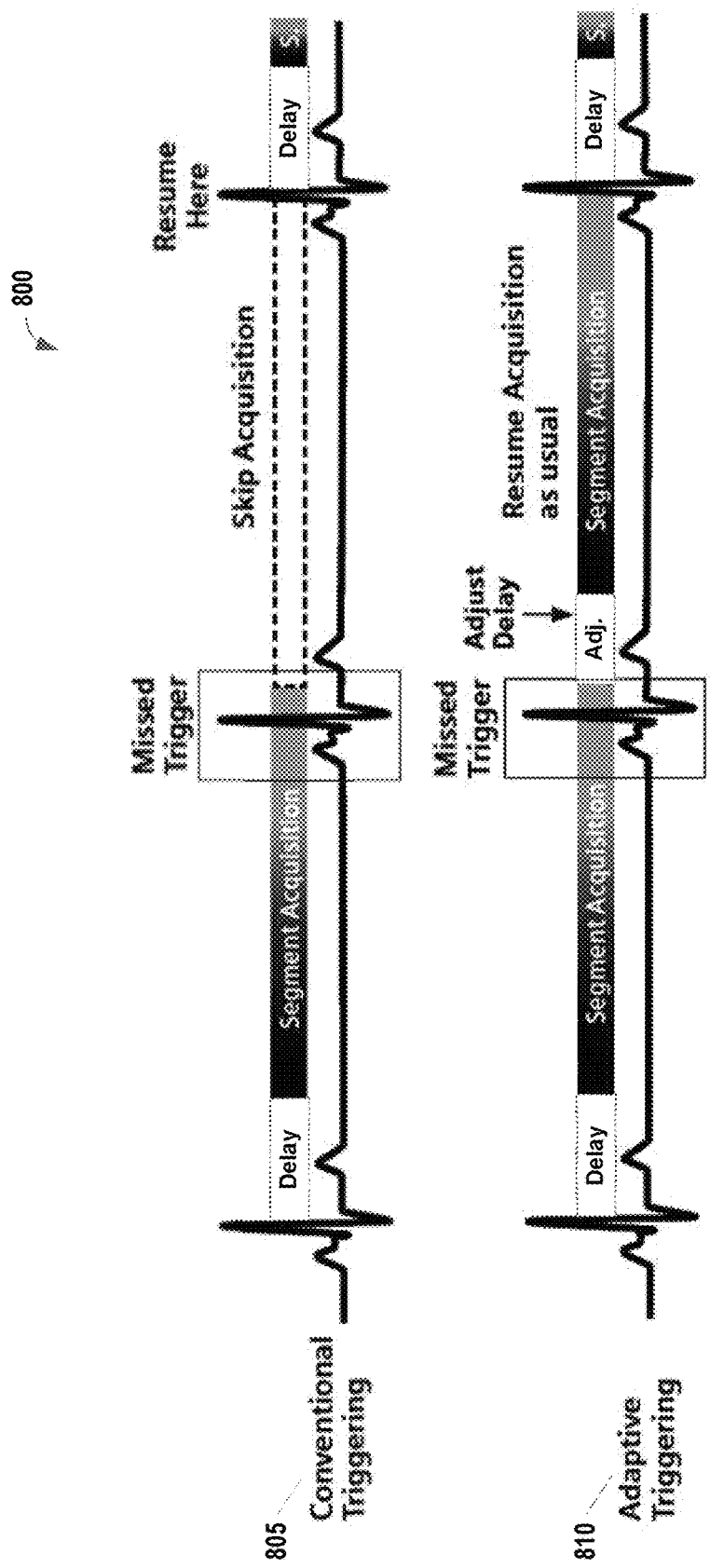
FIG. 8 provides a set of illustrations of how an early trigger case may be handled, according to some embodiments of the present invention.

FIG. 8 provides a set of illustrations 800 of how an early trigger case (e.g., a missed trigger event) may be handled, according to some embodiments of the present invention. In the conventional approach 805, any trigger event that occurs within the acquisition window of the preceding shot is not detected. There are many cases where the R-R interval has been shortened just enough to miss the trigger event (i.e., the early trigger event). The goal of the adaptive approach 810 is to salvage the early trigger event as much as possible and retain the original TD from the trigger event. Once the scan window is completed, the algorithm checks when the trigger event has occurred during the segment acquisition and then calculates the Missed Trigger Time (equal to the delay time since the latest trigger event). If a trigger event is detected during the acquisition, the TD of the next shot will be reduced accordingly.

Figure 9:
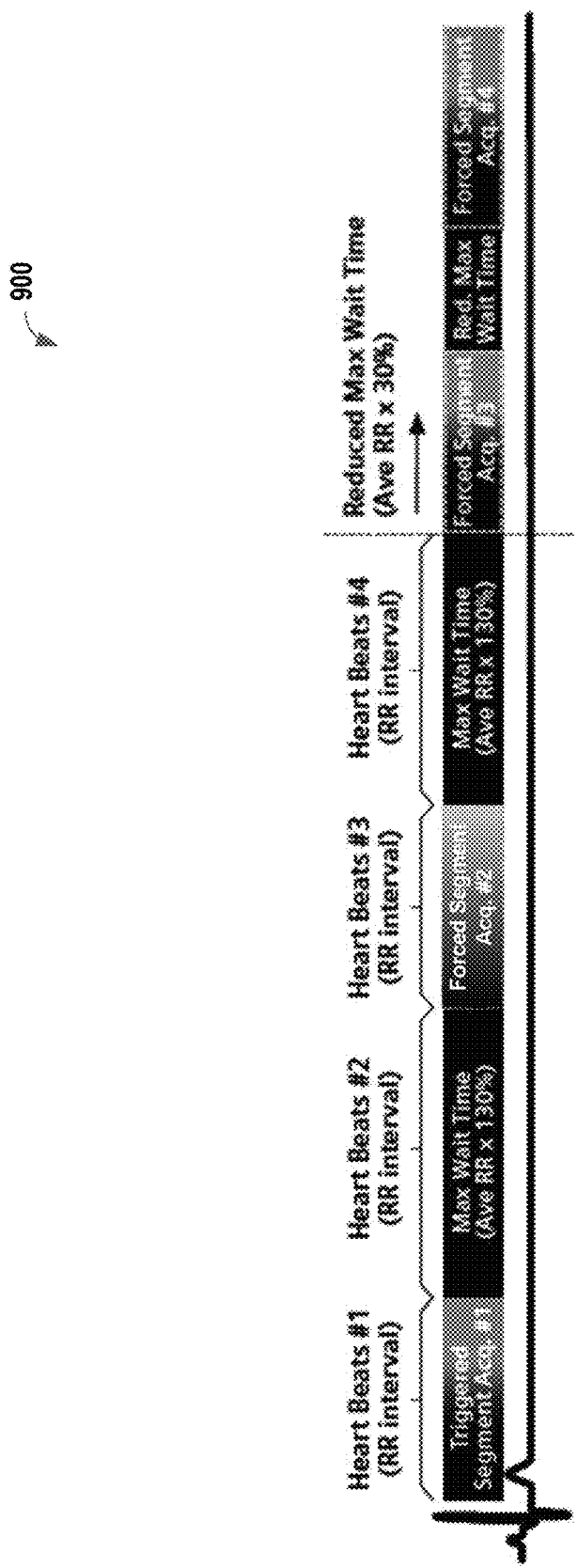
FIG. 9 provides an illustration of how a late trigger case may be handled, according to some embodiments of the present invention.

FIG. 9 provides an illustration 900 of how a late trigger case may be handled, according to some embodiments of the present invention. In order to complete the gated CE-MRA in the case of an ECG trigger failure, a trigger event is enforced after a pre-determined maximum wait time. In this example, after a maximum wait time has elapsed, the trigger event is enforced with TD=0. In some embodiments, this maximum wait time is equal to 130% of the R-R interval. If 2 consecutive maximum wait times (i.e. 4 total heart beats without an event) are observed, the maximum wait time may be shortened (e.g., to 30% of R-R interval) in order to complete the scan within the reasonable time.

From user perspective, the flexible triggered segmentation in the proposed gated CE-MRA translates into an intuitive UI experience. Segmentation and in particularly the duration of a single shot, which affects the overall scan efficiency, has been automatically adjusted according to the subject's heartbeat. The conventional gated CE-MRA, on the other hand, multiple scan parameters such as matrix size, resolution, FOV and PAT factor are required. For TTC per heartbeat (for the specific cardiac phase timing) only one additional UI parameter was required. Other than capturing the cardiac cycle and setting few parameters (trigger delay and TTC per heartbeat), all the other protocol parameters and scan time optimization methods can remain the same as for a standard non-gated CE-MRA protocol.

Figure 10:
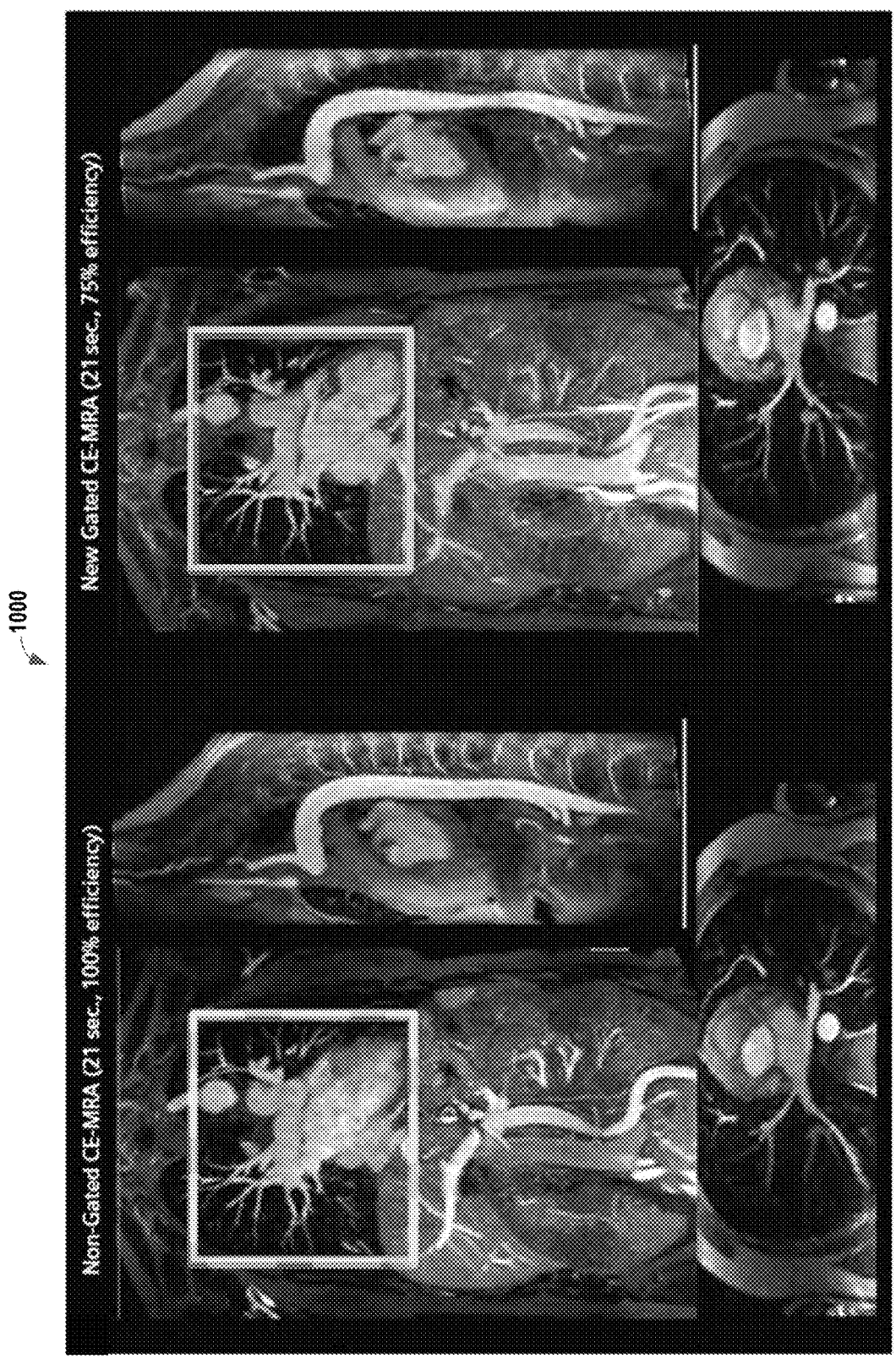
FIG. 10 provides an illustration of a direct comparison of the non-gated versus gated CE-MRA on the same healthy volunteer.

FIG. 10 provides an illustration 1000 of a direct comparison of the non-gated versus gated CE-MRA on the same healthy volunteer. Reformatted thinMIPs of coronal (native acquisition orientation), sagittal and axial orientations are shown. The acquisition parameters are identical, except the gated CE-MRA has few additional parameters in TTC per HB, Acquisition window, and trigger delay. Also the gated CE-MRA has acquired with the elliptical scan to help compensate the efficiency loss.

Figure 11:
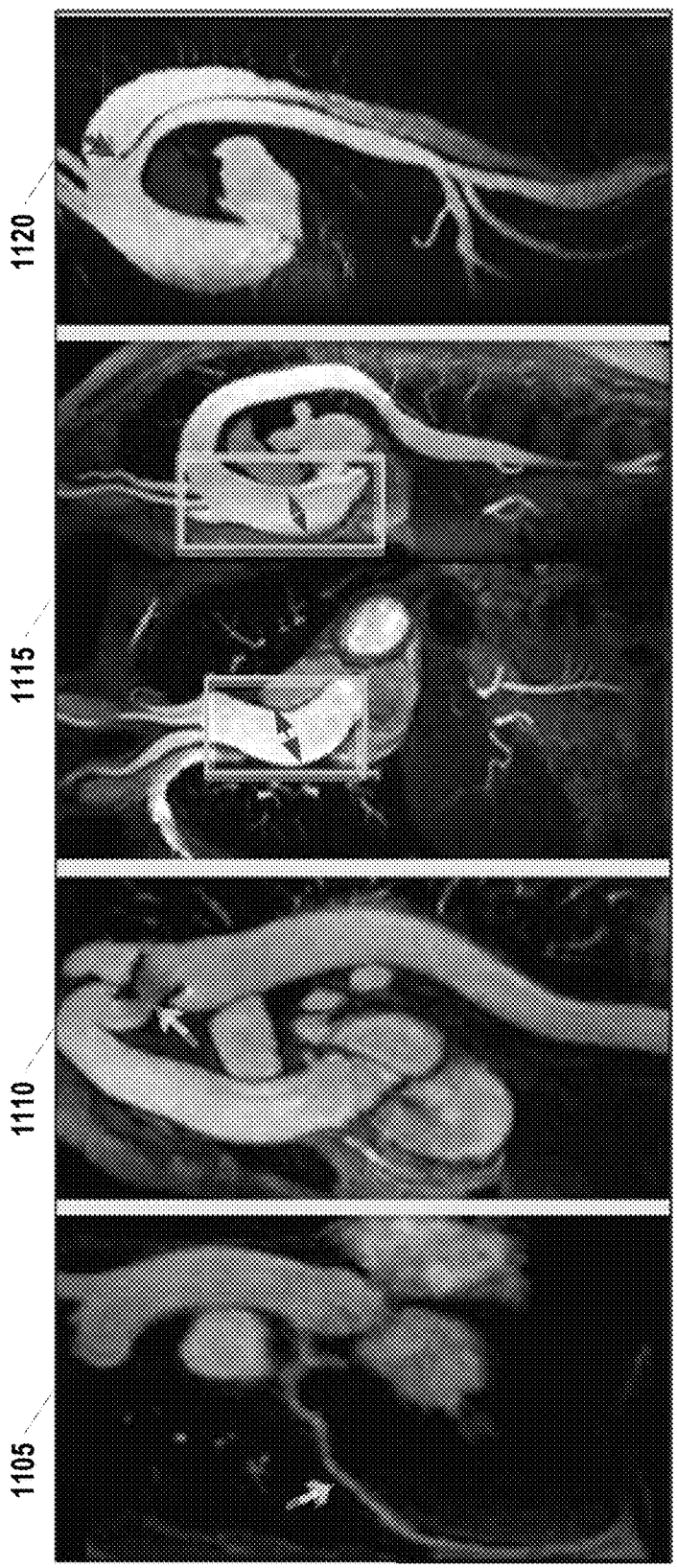
FIGS. 11A, 11B, 11C, and 11D provide various clinical results with the proposed gated CE-MRA, as implemented by some embodiments of the present invention.

FIGS. 11A, 11B, 11C, and 11D provide various clinical results with the proposed gated CE-MRA, as implemented by some embodiments of the present invention. All images are reformatted thin MIPs based on the original coronal acquisition data. FIG. 11A 1105 provides a view of the left arterial descending coronary artery. FIG. 11B provides a view 1110 of the stent lumen narrowing, post repair of aortic coarctation. FIGS. 11C and 11D provide views 1115, 1120 of the dilation of ascending aorta due to aneurism and aortic dissection, respectively. The imaging parameters used in creating FIGS. 11A, 11B, 11C, and 11D are identical to those provided with FIG. 10.

Figure 12:
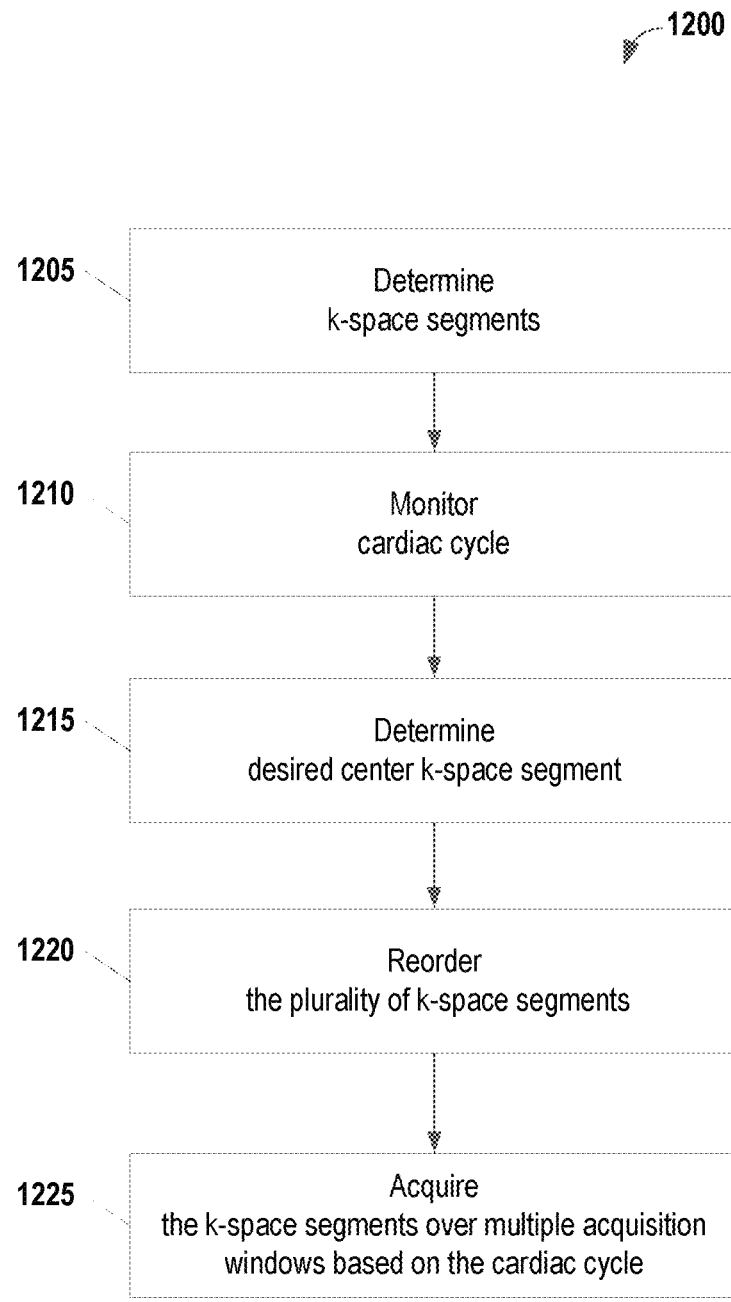
FIG. 12 illustrates a method for using flexible triggered segmentation to optimize magnetic resonance imaging of a patient, according to some embodiments of the present invention.

FIG. 12 illustrates a method 1200 for using flexible triggered segmentation to optimize magnetic resonance imaging of a patient, according to some embodiments of the present invention. At 1205, a plurality of k-space segments is determined, with each respective k-space segment comprising data from multiple dimensions of k-space. In some embodiments, these segments are determined by selecting a predetermined number of elements from a modified k-space table. In one embodiment, this modified k-space table is generated by first applying a segmentation generation function. Then, a scaling algorithm is applied to the resulting k-space table. Next, at 1210 the patient's cardiac cycle is monitored using an electrical signal tracking system such as an ECG system. At 1215, one of the k-space segments is selected as the center k-space segment. In some embodiments, this selection is performed by the user. In other embodiments, the selection may be automatic based on, for example, the timing of a contrast injection into the patient.

Continuing with reference to FIG. 12, at 1220, the k-space segments are reordered such that the center k-space segment selected at 1215 will be acquired during a diastolic phase of the cardiac cycle. In some embodiments, this reordering is performed by a linear-centric reordering process. Then, at 1225, the k-space segments are acquired over a plurality of acquisition windows, with each acquisition window is triggered based on the patent's cardiac cycle. In some embodiments, an early trigger adjustment process may be applied following each acquisition window. For example, each respective acquisition window may have a trigger delay value. If a trigger event occurs during a respective acquisition window and the timing of the event is less than or equal to the trigger delay value, a subsequent trigger delay value associated with a subsequent acquisition window may be adjusted. Similarly, if a subsequent trigger event does not occur within a predetermined maximum wait time (e.g., specified by the user), a subsequent acquisition window may be automatically initiated. Then, following the subsequent acquisition window, if a next trigger event does not occur within the predetermined maximum wait time, a trigger delay value associated with the acquisition windows may be reduced to a predetermined minimal wait time value.

A processor as used herein is a computer, processing device, logic array or other device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The embodiments of the present disclosure may be implemented with any combination of hardware and software components. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately. Further, the processes and applications may, in alternative embodiments, be located on one or more (e.g., distributed) processing devices on a network linking the units of FIG. 1.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. No claim element herein is to be construed under the provisions of 35 U.S.C. 112, sixth paragraph, unless the element is expressly recited using the phrase "means for."

We claim:

1. A method for using flexible triggered segmentation to optimize magnetic resonance imaging, the method comprising:
   partitioning a k-space table into a plurality of k-space segments, each respective k-space segment comprising one or more phase-encoding steps from a plurality of slice-encoding lines;
   monitoring a cardiac cycle using an electrical signal tracking system coupled to a magnetic resonance imaging system;
   using the cardiac cycle to trigger acquisition of the plurality of k-space segments over a plurality of acquisition windows using the magnetic resonance imaging system; and
   generating one or more images based on the acquired plurality of k-space segments,
   wherein the k-space table is partitioned into the plurality of k-space segments by a process comprising:
   applying a segmentation generation function to the k-space table to yield a segmentation generation function table comprising numerical values corresponding to elements in the k-space table;
   applying a scaling algorithm to the segmentation function generation table to yield a modified segmentation generation function table comprising scaled numerical values corresponding to elements in the k-space table; and
   partitioning the modified segmentation generation function table into the plurality of k-space segments based on the scaled numerical values.

2. The method of claim 1, wherein the scaling algorithm comprises:
   multiplying each respective element of the segmentation generation table by a predetermined multiplicator value; and
   adding a pseudo-random number to each respective element of the segmentation generation table.

3. The method of claim 1, further comprising:
   identifying a center k-space segment from the plurality of k-space segments, wherein the center k-space segment comprises lines close to k-space center than at least some lines included in other k-space segments; and
   prior to acquiring the plurality of k-space segments, applying a linear-centric reordering process to the plurality of k-space segments such that the center k-space segment will be acquired during a diastolic phase of the cardiac cycle.

4. The method of claim 3, wherein the center k-space segment is identified by a user.

5. The method of claim 3, wherein the center k-space segment is automatically selected based on timing of a contrast injection.

6. The method of claim 1, further comprising:
following each respective acquisition window, performing an early trigger adjustment process comprising:
determining whether a trigger event occurred during the respective acquisition window,
if the trigger event occurred during the respective acquisition window, determining a missed trigger time value based on a current time value and a time of occurrence of the trigger event,
determining a trigger delay value associated with the respective acquisition window, and
if the missed trigger time value is less than or equal to the trigger delay value, adjusting a subsequent trigger delay value associated with a subsequent acquisition window.

7. The method of claim 1, further comprising:
following each respective acquisition window, if a subsequent trigger event does not occur within a predetermined maximum wait time, automatically initiating a subsequent acquisition window.

8. The method of claim 7, further comprising:
following the subsequent acquisition window, if a next trigger event does not occur within the predetermined maximum wait time, reducing a trigger delay value associated with the plurality of acquisition windows to a predetermined minimal wait time value.

9. The method of claim 1, further comprising:
receiving a time-to-center value from a user interface,
wherein acquisition of each respective k-space segment included in the plurality of k-space segments is timed such a center point of the respective k-space segment occurs at the time-to-center value.

10. A method for using flexible triggered segmentation to optimize magnetic resonance imaging, the method comprising:
determining a plurality of k-space segments, each respective k-space segment comprising data from multiple dimensions of k-space;
monitoring a cardiac cycle using an electrical signal tracking system using a coupled to a magnetic resonance imaging system;
selecting a center k-space segment from the plurality of k-space segments;
applying a linear-centric reordering process to the plurality of k-space segments such that the center k-space segment will be acquired during a diastolic phase of the cardiac cycle;
acquiring the plurality of k-space segments over a plurality of acquisition windows using the magnetic resonance imaging system, wherein each acquisition window is triggered based on the cardiac cycle; and
generating one or more images based on the acquired plurality of k-space segments,
wherein the plurality of k-space segments are determined by a process comprising:
applying a segmentation generation function to the k-space table to yield a segmentation generation function table comprising numerical values corresponding to elements in the k-space table;
applying a scaling algorithm to the segmentation function generation table to yield a modified segmentation generation function table comprising scaled numerical values corresponding to elements in the k-space table; and
partitioning the modified segmentation generation function table into the plurality of k-space segments based on the scaled numerical values.

11. The method of claim 10, wherein the scaling algorithm comprises:
multiplying each respective element of the segmentation generation table by a predetermined multiplicator value; and
adding a pseudo-random number to each respective element of the segmentation generation table.

12. The method of claim 10, wherein the particular center k-space segment is identified by a user.

13. The method of claim 10, wherein the particular center k-space segment is automatically selected based on timing of a contrast injection.

14. The method of claim 10, further comprising:
following each respective acquisition window, performing an early trigger adjustment process comprising:
determining whether a trigger event occurred during the respective acquisition window, if the trigger event occurred during the respective acquisition window, determining a missed trigger time value based on a current time value and a time of occurrence of the trigger event,
determining a trigger delay value associated with the respective acquisition window, and if the missed trigger time value is less than or equal to the trigger delay value, adjusting a subsequent trigger delay value associated with a subsequent acquisition window.

15. The method of claim 10, further comprising:
following each respective acquisition window, if a subsequent trigger event does not occur within a predetermined maximum wait time, automatically initiating a subsequent acquisition window.

16. The method of claim 15, further comprising:
following the subsequent acquisition window, if a next trigger event does not occur within the predetermined maximum wait time, reducing a trigger delay value associated with the plurality of acquisition windows to a predetermined minimal wait time value.

17. The method of claim 10, further comprising:
receiving a time-to-center value from a user interface,
wherein acquisition of each respective k-space segment included in the plurality of k-space segments is timed such a center point of the respective k-space segment occurs at the time-to-center value.

18. A system for using flexible triggered segmentation to optimize magnetic resonance imaging, the system comprising:
an image data processor configured to (i) partition a k-space table into a plurality of k-space segments, each respective k-space segment comprising one or more phase-encoding steps from a plurality of slice-encoding lines, and (ii) generate one or more images based on the acquired plurality of k-space segments;
an electrocardiography device configured to monitor a cardiac cycle using an electrical signal tracking system; and
a Radio Frequency (RF) generator configured to acquire the plurality of k-space segments over a plurality of acquisition windows, wherein each acquisition window is triggered based on the cardiac cycle, wherein the image data processor is configured to partition the k-space table into the plurality of k-space segments by a process comprising:
   applying a segmentation generation function to the k-space table to yield a segmentation generation function table comprising numerical values corresponding to elements in the k-space table;
   applying a scaling algorithm to the segmentation function generation table to yield a modified segmentation generation function table comprising scaled numerical values corresponding to elements in the k-space table; and
   partitioning the modified segmentation generation function table into the plurality of k-space segments based on the scaled numerical values:
wherein the system is configured to trigger acquisition of the plurality of k-space segments over a plurality of acquisition windows based on a signal provided by the electrocardiography device.

* * * * *